(12) United States Patent
Akagane

(10) Patent No.: US 11,602,369 B2
(45) Date of Patent: Mar. 14, 2023

(54) VIBRATION TRANSMITTER AND ULTRASONIC TREATMENT INSTRUMENT

(71) Applicant: OLYMPUS CORPORATION, Hachioji (JP)

(72) Inventor: Tsunetaka Akagane, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 979 days.

(21) Appl. No.: 16/407,754

(22) Filed: May 9, 2019

(65) Prior Publication Data
US 2019/0262027 A1    Aug. 29, 2019

Related U.S. Application Data

(63) Continuation of application No. PCT/JP2016/083229, filed on Nov. 9, 2016.

(51) Int. Cl.
*A61B 17/32* (2006.01)
*A61B 17/00* (2006.01)
(Continued)

(52) U.S. Cl.
CPC ............ *A61B 17/320068* (2013.01); *A61B 17/320092* (2013.01); *A61B 2017/00367* (2013.01); *A61B 2017/2911* (2013.01); *A61B 2017/2927* (2013.01); *A61B 2017/32009* (2017.08); *A61B 2017/320072* (2013.01);
(Continued)

(58) Field of Classification Search
CPC ........... A61B 17/320068; A61B 2017/320073; A61B 2017/320094; A61B 2017/320089; A61B 2017/32009
See application file for complete search history.

(56) References Cited

U.S. PATENT DOCUMENTS

| | | | |
|---|---|---|---|
| 6,790,216 B1* | 9/2004 | Ishikawa | A61B 17/320068 606/169 |
| 2005/0033201 A1* | 2/2005 | Takahashi | A61B 17/320068 601/2 |

(Continued)

FOREIGN PATENT DOCUMENTS

| CN | 104271051 A | 1/2015 |
|---|---|---|
| CN | 104837420 A | 8/2015 |

(Continued)

OTHER PUBLICATIONS

Jan. 28, 2021 Office Action issued in Chinese Application No. 201680090712.4.

(Continued)

*Primary Examiner* — Nicholas W Woodall
(74) *Attorney, Agent, or Firm* — Oliff PLC

(57) ABSTRACT

A vibration transmitter can include a straight portion, a curved portion, a first curved surface provided on an external surface of the curved portion, a second curved surface facing a side opposite to the first curved surface and a first portion provided on the first curved surface. The first portion can extend towards a side opposite to the side toward which the curved portion is curved and a distance between the first portion and an imaginary curved surface can increase from the proximal side toward the distal side, and the imaginary curved surface being parallel with the second curved surface.

11 Claims, 10 Drawing Sheets

(51) Int. Cl.
  *A61B 17/29* (2006.01)
  *A61B 18/00* (2006.01)
(52) U.S. Cl.
  CPC .............. *A61B 2017/320073* (2017.08); *A61B 2017/320089* (2017.08); *A61B 2017/320094* (2017.08); *A61B 2018/00994* (2013.01)

(56) References Cited

U.S. PATENT DOCUMENTS

| | | | |
|---|---|---|---|
| 2006/0100616 A1* | 5/2006 | Beaupre | A61B 17/320068 606/34 |
| 2009/0143806 A1* | 6/2009 | Witt | A61N 7/00 427/2.28 |
| 2012/0116363 A1* | 5/2012 | Houser | A61B 46/10 606/1 |
| 2013/0289592 A1 | 10/2013 | Stulen et al. | |
| 2014/0163595 A1 | 6/2014 | Witt et al. | |
| 2016/0175001 A1* | 6/2016 | Hibner | A61B 17/320092 606/28 |
| 2016/0242806 A1* | 8/2016 | Akagane | A61B 17/22004 |

FOREIGN PATENT DOCUMENTS

| | | |
|---|---|---|
| JP | 2015-516231 A | 6/2015 |
| JP | 2015-536760 A | 12/2015 |
| WO | 2016/171067 A1 | 10/2016 |

OTHER PUBLICATIONS

May 14, 2019 Translation of International Preliminary Report on Patentability issued in International Patent Application No. PCT/JP2016/083229.

Feb. 7, 2017 Intenrational Search Report issued in International Patent Application No. PCT/JP2016/083229.

Jul. 1, 2021 Office Action issued in Chinese Application No. 201680090712.4.

* cited by examiner

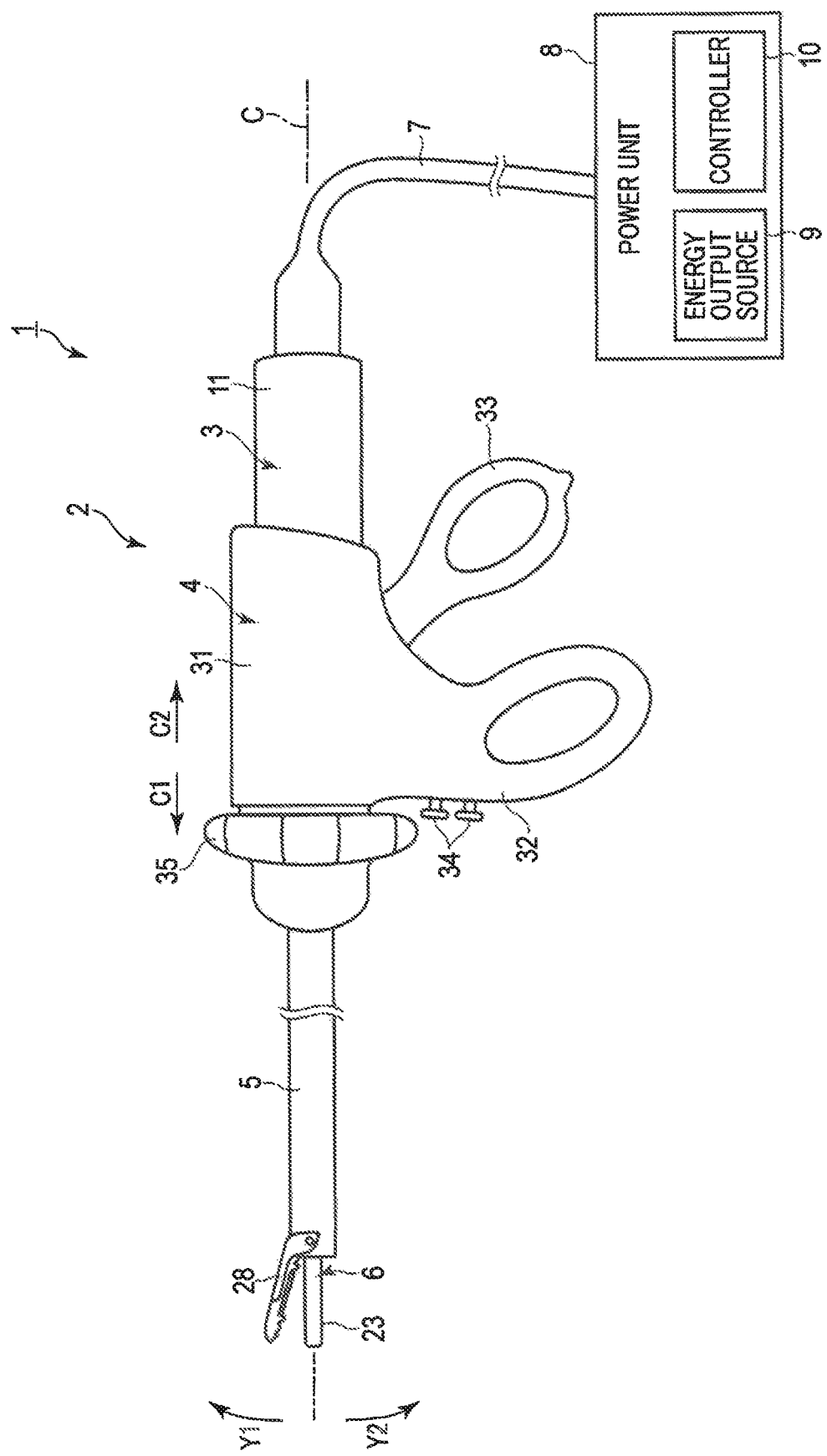
F I G. 1

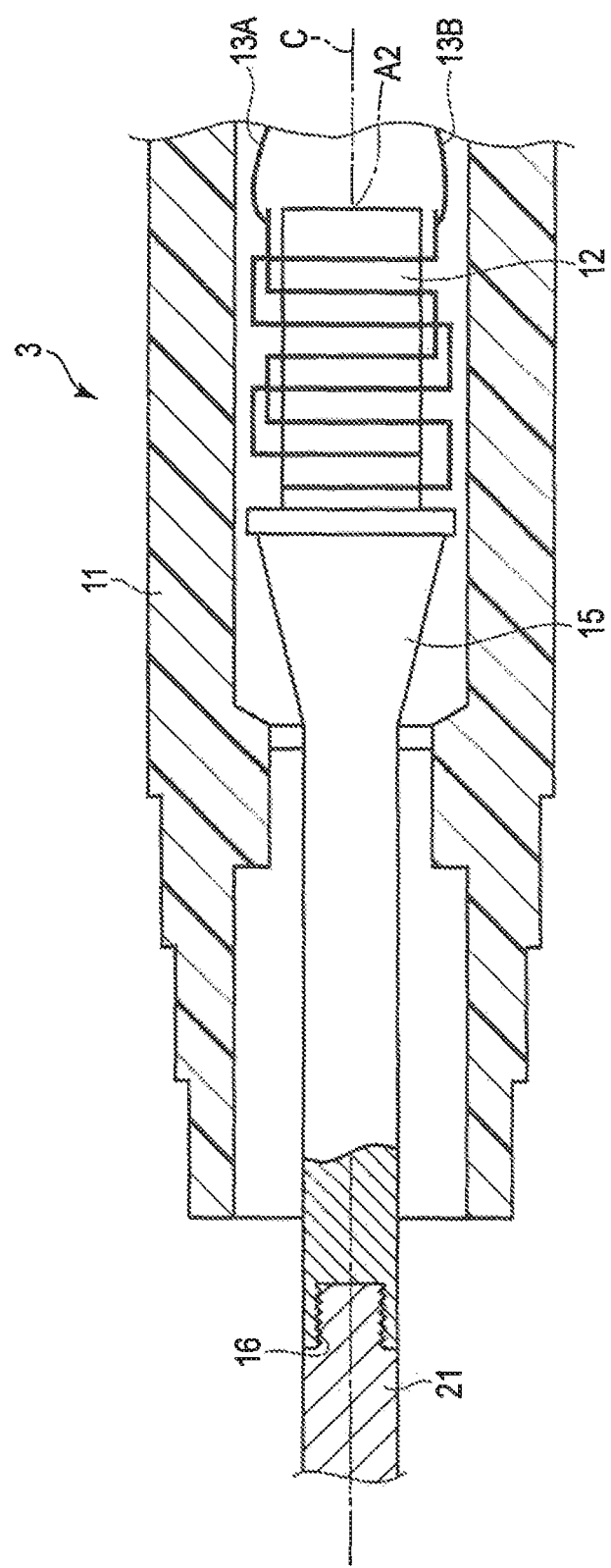
F I G. 2

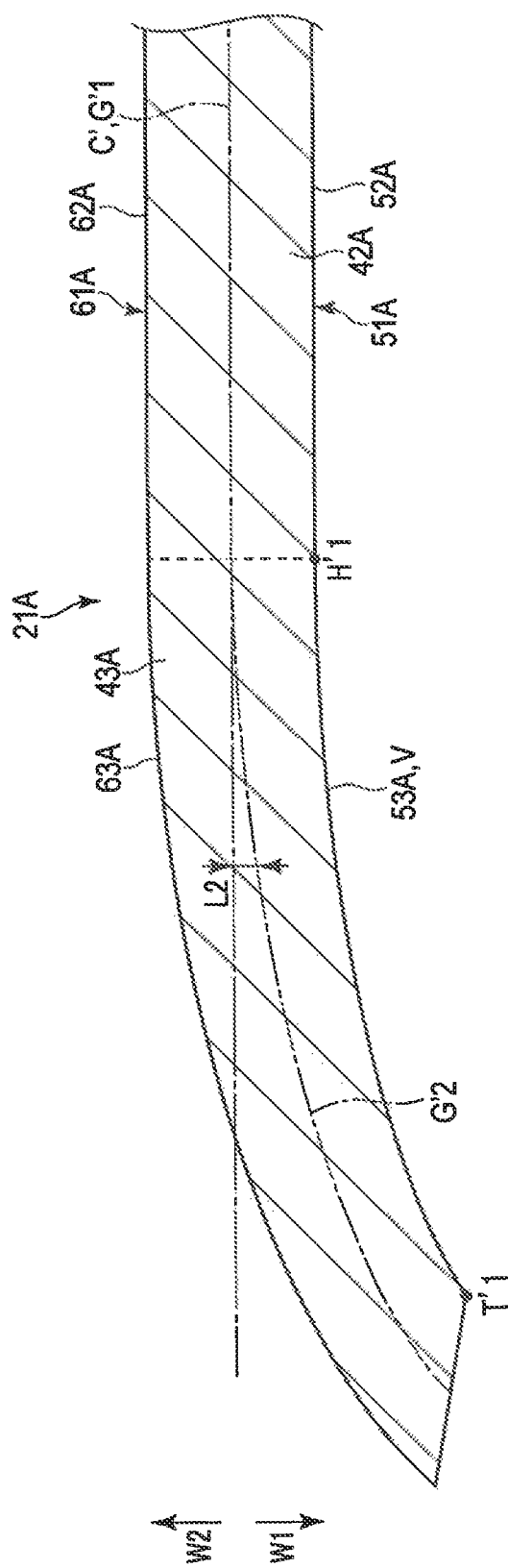
F I G. 6

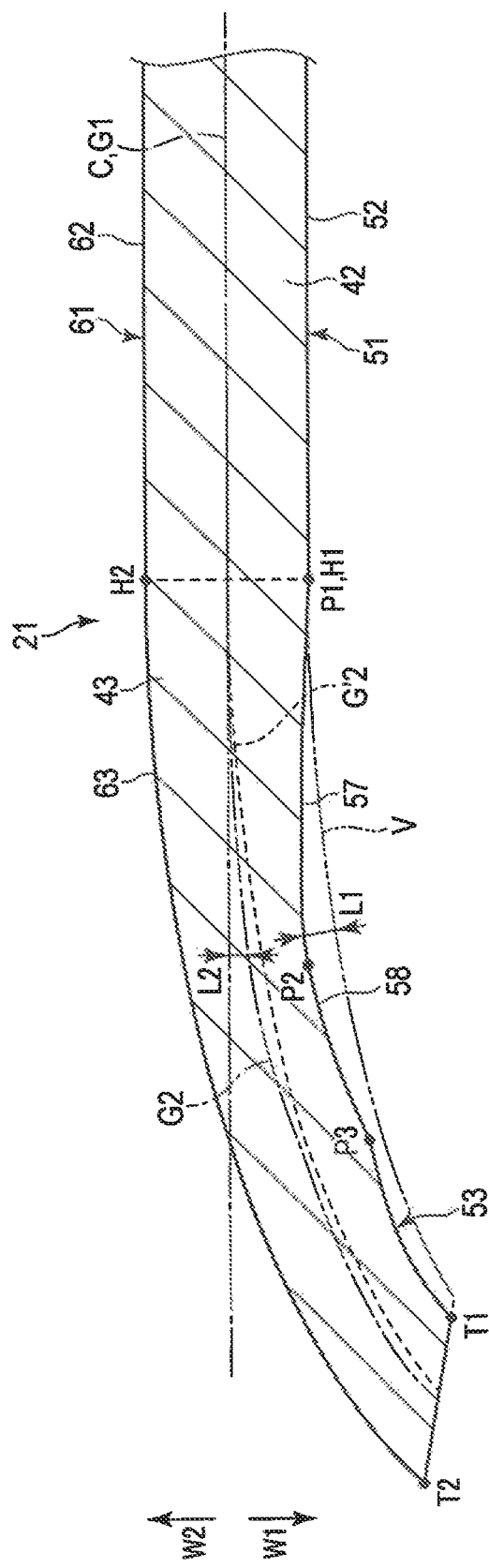
F I G. 11

VIBRATION TRANSMITTER AND ULTRASONIC TREATMENT INSTRUMENT

CROSS-REFERENCE TO RELATED APPLICATIONS

This is a Continuation Application of PCT Application No. PCT/JP2016/083229, filed Nov. 9, 2016, the entire contents of which are incorporated herein by reference.

BACKGROUND

An ultrasonic treatment instrument for treating a treated target grasped between a pair of grasping pieces using ultrasonic vibrations can include an ultrasonic probe serving as a vibration transmitter extended along a longitudinal axis and transmitting ultrasonic vibrations from the proximal side to the distal side. One of the grasping pieces can be formed of a distal portion of the ultrasonic probe. The ultrasonic probe can include a straight portion extended along the longitudinal axis. The distal portion of the ultrasonic probe can be provided with a curved portion curved toward a direction substantially perpendicular to the longitudinal axis.

SUMMARY

A vibration transmitter can transmit ultrasonic vibrations from a proximal end to a distal end of the vibration transmitter. The vibration transmitter can include a straight portion on a proximal side and a curved portion provided on a distal side. The curved portion can be curved in a direction that intersects a longitudinal axis of the vibration transmitter. A first curved surface can be provided on a first surface of the curved portion that faces a side toward which the curved portion is curved, a second curved surface provided on a second surface of the curved portion that faces a side opposite to the side toward which the curved portion is curved. A first portion can be provided on the first curved surface, the first portion can extend towards the side opposite to the side toward which the curved portion is curved from an imaginary curved surface that is parallel with the second curved surface.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a schematic diagram illustrating an ultrasonic treatment system according to an exemplary embodiment;

FIG. 2 is a cross-sectional view schematically illustrating a structure of a vibrator unit according to an exemplaryembodiment;

FIG. 6 is a cross-sectional view schematically illustrating a distal portion of a probe according to an exemplary embodiment;

FIG. 11 is cross-sectional view schematically illustrating a distal portion of a probe.

DETAILED DESCRIPTION OF THE INVENTION

Figure 3:
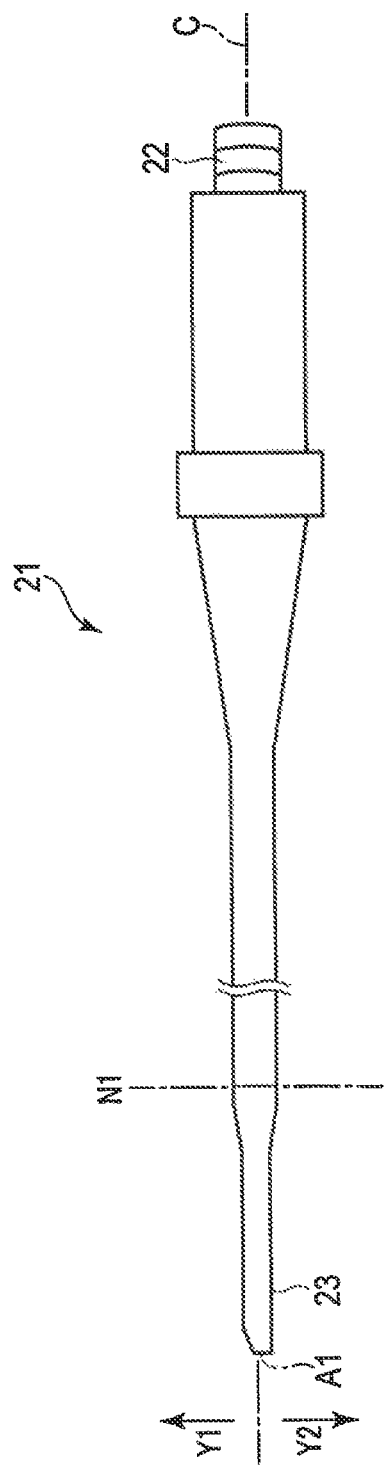
FIG. 3 is a diagram schematically illustrating a probe according to an exemplaryembodiment.

FIG. 1 is a diagram illustrating an ultrasonic treatment system 1 according to the present embodiment. As illustrated in FIG. 1, the ultrasonic treatment system 1 includes an energy treatment instrument 2. The energy treatment instrument 2 serves as an ultrasonic treatment instrument in the present embodiment. In the energy treatment instrument 2, a longitudinal axis C is defined, and a direction extending along the longitudinal axis C is defined as a longitudinal direction. In addition, one side of the longitudinal direction is referred to as distal side (arrow C1 side), and a side opposite to the distal side is referred to as proximal side (arrow C2 side). The longitudinal axis C is a substantially straight axis extending from the proximal side to the distal side.

The energy treatment instrument 2 includes a housing 4 that can be held, a shaft 5 connected with the distal side of the housing 4, and an end effector 6 provided at a distal portion of the shaft 5. A vibrator unit 3 is connected with a proximal side of the housing 4. The vibrator unit 3 includes a vibrator case 11. A proximal end of the vibrator case 11 is connected with one end of a cable 7. The other end of the cable 7 is detachably connected with a power unit 8.

The power unit 8 includes an energy output source 9 and a controller 10. The energy output source 9 includes a converter circuit or the like converting electric power from a battery power source or a socket power source into electric energy (alternating current power) to be supplied to the vibrator unit 3, and outputs the converted electric energy. The controller 10 includes an integrated circuit including a CPU (Central Processing Unit), an ASIC (Application Specific Integrated Circuit) or a FPGA (Field Programmable Gate Array), or a processor, and a storage medium.

The housing 4 includes a cylindrical case 31 extended along the longitudinal axis C. The vibrator case 11 is inserted into the cylindrical case 31 from the proximal side, and thereby the vibrator unit 3 is connected with the housing 4.

A grip (fixed handle) 32 is extended from the cylindrical case 31. A handle (movable handle) 33 is rotatably attached to the cylindrical case 31. By rotation of the handle 33 with respect to the cylindrical case 31, the handle 33 is opened or closed with respect to the grip 32. In the present embodiment, the handle 33 is located on the proximal side with respect to the grip 32, and moves in substantially parallel with the longitudinal axis C in an opening/closing operation with respect to the grip 32, but the structure is not limited thereto. For example, in an embodiment, the handle 33 may be located on the distal side with respect to the grip 32. In another embodiment, the handle 33 may be located on a side opposite to the grip 32 with respect to the longitudinal axis C, and the moving direction thereof in an opening/closing operation with respect to the grip 32 may cross (or may be substantially perpendicular to) the longitudinal axis C.

Operating buttons 34 serving as an energy operation input unit are attached to the housing 4. By pressing the operating buttons 34, an operation (signal) is input to the power unit 8, to cause the power unit 8 to output electric energy from the energy output source 9 to the energy treatment instrument 2. Instead of or in addition to the operating buttons 34, a foot switch or the like serving as a unit separated from the energy treatment instrument 2 may be provided as the energy operation input unit.

FIG. 2 is a diagram illustrating a structure of the vibrator unit 3. As illustrated in FIG. 2, an ultrasonic transducer 12 is provided inside the vibrator case 11. The ultrasonic transducer 12 includes a piezoelectric element converting supplied electric energy into ultrasonic vibrations. The ultrasonic transducer 12 is connected with one ends of electric signal lines 13A and 13B. The electric signal lines 13A and 13B extend through the inside of the cable 7, and the other ends of thereof are connected with the energy output source 9 of the power unit 8. A current (alternating current) is supplied to the ultrasonic transducer 12 from the energy output source 9 through the electric signal lines 13A and 13B, to generate ultrasonic vibrations in the ultrasonic transducer 12. A columnar horn 15 is attached to the ultrasonic transducer 12. A female screw portion 16 is formed at the distal portion of the horn 15. A probe 21 is attached to the distal side of the horn 15.

FIG. 3 is a diagram illustrating the probe 21. As illustrated in FIG. 3, the probe 21 is extended from the distal side toward the proximal side. A male screw portion 22 is provided at the proximal portion of the probe 21. The male screw portion 22 is engaged with the female screw portion 16 of the horn 15. In this manner, the probe 21 is attached to the horn 15.

By attachment of the probe 21 to the horn 15, ultrasonic vibrations generated in the ultrasonic transducer 12 are transmitted to the distal end of the probe 21 through the horn 15. In this state, the probe 21 is longitudinally (vertically) vibrated by the ultrasonic vibrations in a direction parallel with the longitudinal axis C. Specifically, the probe 21 is a vibration transmitter capable of transmitting ultrasonic vibrations from the proximal side to the distal side. The probe (ultrasonic probe) 21 is formed of a material with high vibration transmissibility, such as titanium alloy. Examples of the titanium alloy forming the probe 21 include 64 titanium (Ti-6AI-4V).

The shaft 5 is extended along the longitudinal axis C. The shaft 5 is inserted into the cylindrical case 31 from the distal side, and connected with the housing 4. The shaft 5 is also connected with the vibrator case 11 inside the cylindrical case 31. The probe 21 is inserted through the shaft 5. The distal portion of the probe 21 projects from the distal end of the shaft 5 toward the distal side. A projecting portion of the probe 21 projecting from the distal end of the shaft 5 forms a treatment portion 23 at the distal portion of the probe 21.

The end effector 6 is formed of the treatment portion 23 and a jaw 28 opened and closed with respect to the treatment portion 23. The jaw 28 is rotatably attached to the distal portion of the shaft 5. The jaw 28 is connected with the handle 33 through a movable member (not illustrated) extending inside the shaft 5 along the longitudinal axis C. By opening or closing the handle 33 serving as the opening/closing operation input unit with respect to the grip 32, the movable member moves along the longitudinal axis C with respect to the shaft 5 and the housing 4, and the jaw 28 is opened or closed with respect to the treatment portion 23. By closure of the jaw 28 with respect to the treatment portion 23, a living tissue, such as a blood vessel, is grasped as a treated target between the treatment portion 23 and the jaw 28. Specifically, the jaw 28 and the treatment portion 23 functions as a pair of grasping pieces.

The opening/closing directions of the end effector 6 cross (are substantially perpendicular to) the longitudinal axis C. In the opening/closing directions of the end effector 6, the side in which the jaw 28 is opened with respect to the treatment portion 23 is referred to as opening direction side (arrow Y1 side in FIG. 1) of the jaw 28, and the side in which the jaw 28 is closed with respect to the treatment portion 23 is referred to as closing direction side (arrow Y2 side in FIG. 1) of the jaw 28.

The housing 4 also includes a rotating operation knob 35 serving as a rotating operation input unit connected with the distal side of the cylindrical case 31. The rotating operation knob 35 is connected with the cylindrical case 31 rotatably with respect to the cylindrical case 31 around the longitudinal axis C. By rotation of the rotating operation knob 35 with respect to the cylindrical case 31, the probe 21, the shaft 5, and the jaw 28 are rotated around the longitudinal axis C with respect to the cylindrical case 31.

The probe 21 and the horn 15 vibrate in a predetermined vibration mode (vibration state) used in treatment, by transmission of ultrasonic vibrations generated in the ultrasonic transducer 12. In the predetermined vibration mode, the probe 21 and the horn 15 longitudinally vibrate in a vibration direction substantially parallel with the longitudinal axis C. In the predetermined vibration mode, antinodes of the longitudinal vibrations are positioned at the distal end of the probe 21 and the proximal end of the ultrasonic transducer 12 (proximal end of the horn 15). The antinode A1 positioned at the distal end of the probe 21 is the most distal antinode in the antinodes. The antinode A2 positioned at the proximal end of the horn 15 is the most proximal antinode in the antinodes. In the predetermined vibration mode, each of the number of antinodes and the number of nodes between the distal end of the probe 21 and the proximal end of the ultrasonic transducer 12 is a predetermined number, and at least one node exists between the distal end of the probe 21 and the proximal end of the ultrasonic transducer 12 (proximal end of the horn 15). The controller 10 regulates the frequency of the electric energy (alternating current) supplied to the ultrasonic transducer 12, to regulate the resonance frequency of a vibrator formed of the ultrasonic transducer 12, the horn 15, and the probe 21. In this manner, the controller 10 causes the vibrator unit 3 to longitudinally vibrate in the predetermined vibration mode. The number of nodes and the number of antinodes of longitudinal vibration in the predetermined vibration mode are determined in accordance with the longitudinal size of the vibration unit 3 and the resonance frequency of ultrasonic vibrations used for treatment, and the like.

Figure 4:
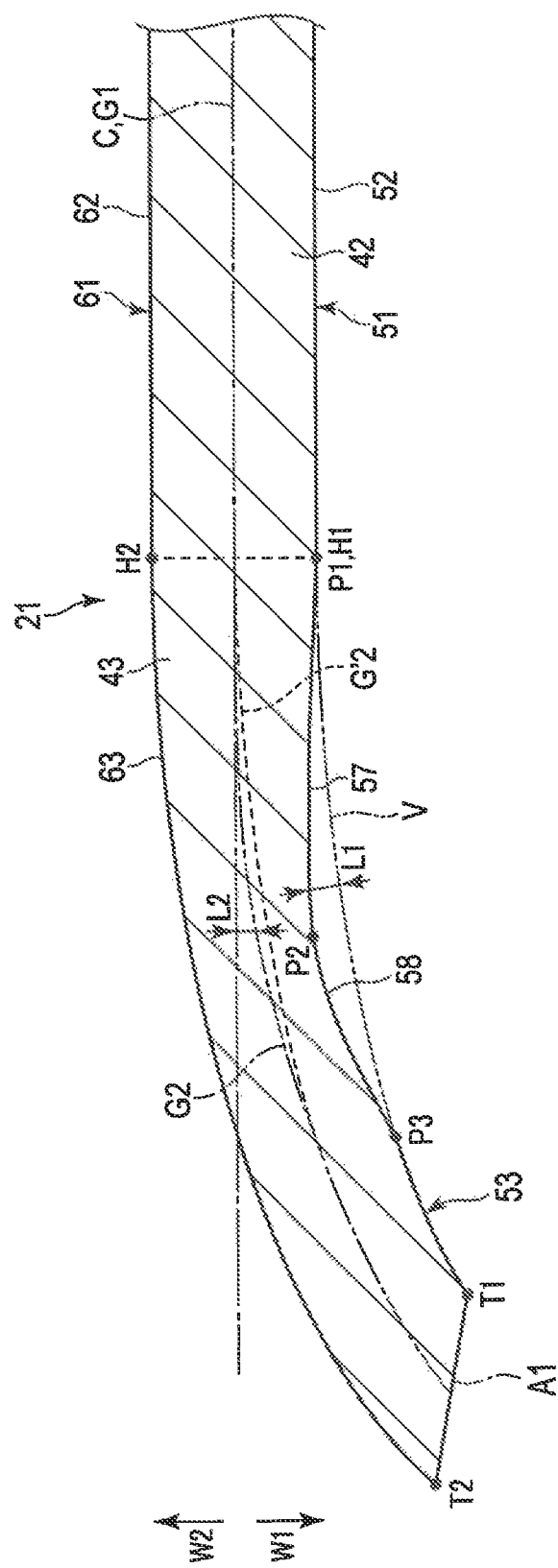
FIG. 4 is a cross-sectional view schematically illustrating a distal portion of the probe according to an exemplaryembodiment.

FIG. 4 is a diagram illustrating the distal portion of the probe 21 at a cross section crossing (substantially perpendicular to) the opening/closing directions of the end effector 6. The directions crossing (substantially perpendicular to) the opening/closing directions of the end effector 6 and the longitudinal direction serve as width directions of the probe 21. One of the width directions of the probe 21 serves as a first width direction side (arrow W1 side of FIG. 4). The direction opposite to the first width direction serves as a second width direction side (arrow W2 side of FIG. 4).

As illustrated in FIG. 4, the probe 21 includes a straight portion 42 extended along the longitudinal axis C. The straight portion 42 is extended substantially straight. The longitudinal axis C extends through the center of the straight portion 42. In the present embodiment, the portion from the proximal end of the probe 21 to a part of the projecting portion (treatment portion 23) projecting from the distal end of the shaft 5 serves as the straight portion 42 that is substantially straight. In another embodiment, the portion of the probe 21 extended from the distal position of the shaft 5 (proximal end of the treatment portion 23) to a part of the treatment portion 23 serves as the straight portion 42.

The distal end portion of the probe 21 is provided with a curved portion 43. The curved portion 43 is curved in one direction (first direction side) crossing the longitudinal axis C with respect to the straight portion 42. In the present embodiment, the curved portion 43 is curved in the first width direction side with respect to the straight portion 42. Accordingly, the curved portion 43 is extended in a state of going toward the first width direction side as it extends from the proximal side toward the distal side. Specifically, the first width direction serves as the curved direction of the curved portion 43.

Figure 5:
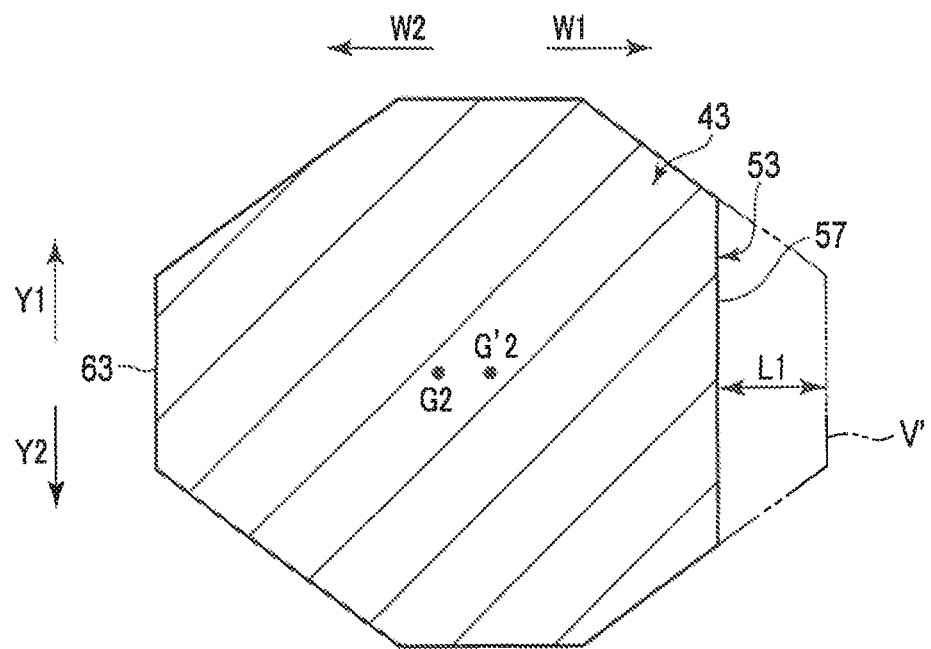
FIG. 5 is a diagram schematically illustrating a curved portion according to an exemplaryembodiment at a cross section substantially perpendicular to an extending direction of the curved portion.

FIG. 5 is a diagram illustrating a cross section crossing (substantially perpendicular to) the extending direction of the curved portion 43, in the curved portion 43. As illustrated in FIG. 4 and FIG. 5, a surface facing the first width direction side in the external surfaces of the probe 21 is referred to as first side surface 51. The first side surface 51 is positioned on the first width direction side of the center of the probe 21. In addition, in the external surfaces of the probe 21, a surface facing the second width direction side is referred to as second side surface 61. The second side surface 61 is formed on the external surface facing a side opposite to the first side surface 51 in the probe 21. The second side surface 61 is positioned on the second width direction side of the center of the probe 21.

The first side surface 51 includes an extended surface 52 facing the first width direction side in the straight portion 42, and a curved surface portion 53 facing the first width direction side in the curved portion 43. In the present embodiment, the curved surface portion 53 serves as a first curved surface provided on the external surface of the curved portion 43 and facing the first direction side (first width direction side). The curved surface portion 53 has a curved line in which at least part of the curved surface portion 53 is curved toward the first width direction side with respect to the longitudinal axis C, in a cross section running along the longitudinal axis C and the width direction of the probe 21. In addition, the curved surface portion 53 serves as the external surface inside the curve of the curved portion 43.

The second side surface 61 includes an extended surface 62 facing the second width direction side in the straight portion 42, and a curved surface portion 63 facing the second width direction side in the curved portion 43. In the present embodiment, the curved surface portion 63 serves as a second curved surface provided on the external surface of the curved portion 43 and facing a side (second width direction side) opposite to the side (first direction side) toward which the curved portion 43 is curved. Specifically, the second curved surface (63) faces to a side opposite to the first curved surface (53). In addition, the curved surface portion 63 serves as the external surface outside the curve of the curved portion 43. The curved surface portion 63 serves as an arc-shaped curve that is curved toward the first width direction side with respect to the longitudinal axis C and extended through a reference position H2, in a cross section running along the longitudinal axis C and the width direction of the probe 21. In addition, the arc shape of the curve has a center on the first width direction side (inside of the curve) with respect to the probe 21.

A reference position H2 is defined in the second side surface 61. The reference position H2 is a proximal position of the curved portion 43 in the second side surface 61. The reference position H2 serves as a curve start position at which the curved portion 43 starts to curve in the first width direction, and a boundary position between the curved portion 43 and the straight portion 42. Specifically, the reference position H2 serves as a curve start position at which the curved surface portion 63 starts to curve in the first width direction, and a boundary position between the curved surface portion 63 and the extended surface 62. A curve distal end T2 is defined in the second side surface 62. The curve distal end T2 serves as a distal position of the curved portion 43 in the second side surface 61.

In addition, a reference position H1 is defined in the first side surface 51. The reference position H1 and the reference position H2 are located on the same plane crossing (substantially perpendicular to) the longitudinal axis C. Accordingly, the plane extending through the reference position H1 and the reference position H2 is substantially perpendicular to the longitudinal axis C. Specifically, the reference position H1 serves as a proximal position of the curved portion 43 in the first side surface 51. A curve distal end T1 is defined in the first side surface 51. The curve distal end T1 serves as a distal position of the curved portion 43 in the first side surface 51.

An imaginary curved surface V serving as an imaginary curved surface is provided herein. The imaginary curved surface V is extended from the reference position H1 toward the distal side, and extended in parallel with the curved surface portion 63. Specifically, the imaginary curved surface V is curved with respect to the straight portion 42, in a state of going away from the straight portion 42 toward the first width direction side as it extends from the proximal side to the distal side. As illustrated in FIG. 4 and FIG. 5, in a cross section extending along the longitudinal direction and the width direction of the probe 21, the imaginary curved surface V serves as an arc-shaped imaginary curved line (imaginary line) parallel with the curved surface portion 63 and extended through the reference position H1. The arc shape of the imaginary curve has a center on the first width direction side (inside of the curve) of the probe 21. In the present embodiment, the central point of the arc shape formed with the imaginary curved surface V agrees with the central point of the arc shape formed with the curved surface portion 63, and the distance of the arc shape formed with the imaginary curved surface V from the central point is smaller than the distance of the arc shape formed with the curved surface portion 63 from the central point.

Suppose that a distance L1 is a distance between the first side surface 51 (curved surface portion 53) and the imaginary curved surface V in a direction crossing (substantially perpendicular to) the extended direction of the curved portion 43. The curved surface portion 53 and the imaginary curved surface V extend through the reference position H1. For this reason, at the reference position H1, the distance L1 between the curved surface portion 53 and the imaginary curved surface V is 0.

The curved surface portion 53 includes a first portion 57 extended on a side opposite to the side toward which the curved portion 43 is curved with respect to the imaginary curved surface V. In the first portion 57, the distance L1 between the curved surface portion 53 and the imaginary curved surface V increases as the curved surface portion 53 extends from the proximal side toward the distal side. FIG. 5 illustrates a cross section crossing the extended direction of the curved portion 43 and running through a certain position of the first portion 57. In the present embodiment, the first portion 57 is provided over the whole curved surface portion 53 in the opening/closing directions of the end effector 6. Specifically, the first portion 57 is provided over the whole curved portion 43 (curved surface portion 53) in a direction crossing the curved direction of the curved portion 43 and the longitudinal axis C. The proximal position of the first portion 57 is referred to as position P1, and the distal position of the first portion 57 is referred to as position P2. In the present embodiment, the position P1 substantially agrees with the reference position H1. Accordingly, the first portion 57 is extended from the reference position H1 to the position P2. The first portion 57 is positioned on the second width direction side (outside of the curve) of the imaginary curved surface V, in a portion other than the proximal position (reference position H1).

The curved surface portion 53 also includes a second portion 58 extended on a side opposite to the side toward which the curved portion 43 is curved with respect to the imaginary curved surface V. In the second portion 58, the distance L1 between the curved surface portion 53 and the imaginary curved surface V decreases as the curved surface portion 53 extends from the proximal side toward the distal side. The second portion 58 is provided on a distal side of the first portion 57. In the present embodiment, the second portion 58 is provided over the whole curved surface portion 53 in the opening/closing directions of the end effector 6. Specifically, the second portion 58 is provided over the whole curved portion 43 (curved surface portion 53) in a direction crossing the curved direction of the curved portion 43 and the longitudinal axis C. In the present embodiment, the position P2 serving as the distal position of the first portion 57 serves as a proximal position of the second portion 58. Specifically, the second portion 58 is provided to connect the distal side of the first portion 57. In addition, the distal position of the second portion 58 is referred to as position P3. The second portion 58 is extended from the position P2 to the position P3. In the present embodiment, the position P3 is located on the imaginary curved surface V. For this reason, at the position P3, the distance L1 between the curved surface portion 53 and the imaginary curved surface V is 0. The second portion 58 is located on the second width direction side (outside of the curve) of the imaginary curved surface V, in a portion other than the distal position (position P3).

In a portion between the position P3 and the curve distal end T1, the curved surface portion 53 is substantially parallel with the curved surface portion 63. In addition, the position P3 is located on the imaginary curved surface V. For this reason, in the portion between the position P3 and the curve distal end T1, the curved surface portion 53 substantially agrees with the imaginary curved surface V. Accordingly, in the portion between the position P3 and the curve distal end T1, the distance L1 between the curved surface portion 53 and the imaginary curved surface V is 0.

As described above, the distance L1 from the imaginary curved surface V to the curved surface portion 53 on the side opposite to the side toward which the curved portion 43 is curved increases in the first portion 57 as the first portion 57 extends from the position P1 (H1) to the distal side, and becomes maximum at the position P2. In addition, the distance L1 decreases in the second portion 58 as the second portion 58 extends from the position P2 toward the distal side, and becomes 0 again at the position P3. Thereafter, the distance L1 is fixed (0) from the position P3 to the curve distal end T1.

Besides, as described above, the antinode A1 of longitudinal vibrations is positioned at the distal end of the probe 21, in the predetermined vibration mode. The node located at the most distal side in the nodes of longitudinal vibrations in the predetermined vibration mode is referred to as node N1. As illustrated in FIG. 3, in the predetermined vibration mode, the node N1 is positioned on the proximal side of the treatment portion 23 in the probe 21. Specifically, the node N1 is positioned inside the shaft 5.

The following is an explanation of functions and effects of the ultrasonic treatment system 1 according to the present embodiment. When treatment is performed using the ultrasonic treatment system 1, the operator holds the housing 4 of the energy treatment instrument 2 to insert the end effector 6 of the body cavity, such as the abdominal cavity. Thereafter, a living tissue, such as the blood vessel, is disposed between the jaw 28 and the treatment portion 23, and the handle 33 is closed with respect to the grip 32. In this manner, the jaw 28 is closed with respect to the treatment portion 23, and the treated target, such as the living tissue, is grasped between the jaw 28 and the treatment portion 23.

In this state, the operating buttons 34 are pressed. In this manner, electric energy is output from the energy output source 9, and ultrasonic vibrations are generated in the ultrasonic transducer 12. In addition, the probe 21 is longitudinally vibrated in a direction parallel with the longitudinal axis C, and the ultrasonic vibrations are transmitted to the treatment portion 23 provided at the distal portion of the probe 21. Frictional heat generated by ultrasonic vibrations of the treatment portion 23 coagulates and incises the living tissue grasped between the treatment portion 23 and the jaw 28. Specifically, the treatment portion 23 serves as an ultrasonic treatment portion treating a treated target, such as the living tissue, using the transmitted ultrasonic vibrations.

Figure 7:
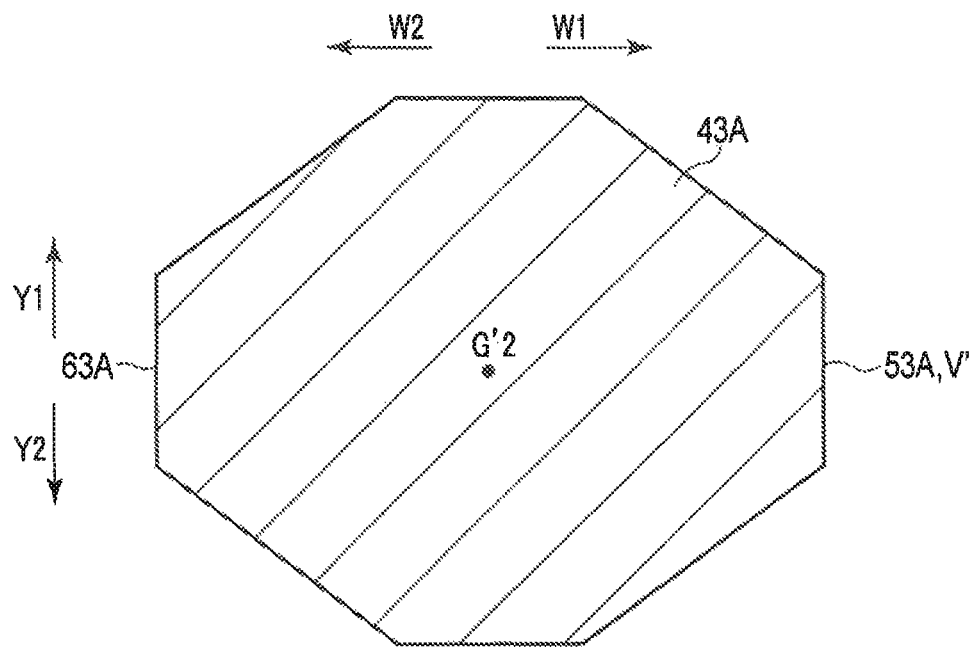
FIG. 7 is a diagram schematically illustrating a curved portion according to an exemplary embodiment at a cross section substantially perpendicular to the extending direction.

FIG. 6 is a diagram illustrating a distal portion of a probe 21A serving as a vibration transmitter in a comparative example of the present embodiment. FIG. 6 illustrates the distal portion of the probe 21A in a cross section extending along the longitudinal direction and the width direction of the probe 21A. FIG. 7 is a diagram illustrating a curved portion 43A in a cross section crossing (substantially perpendicular to) the extended direction of the curved portion 43A. As illustrated in FIG. 6 and FIG. 7, the probe 21A includes a straight portion 42 and a curved portion 43A, and a first side surface 51A and a second side surface 61A are formed on external surfaces of the probe 21A. The first side surface 51A includes an extended surface 52A and a curved surface portion 53A, and the second side surface 61A includes an extended surface 62A and a curved surface portion 63A. The curved surface portion 53A can be provided without a first portion (57) or second portion (58). For this reason, the curved surface portion 53A is formed in substantially parallel with the curved surface portion 63A from a reference position H'1 to a curve distal end T'1. Accordingly, the curved surface portion 53A substantially agrees with an imaginary curved surface V'. Specifically, the imaginary curved surface V'1 extends through the reference position H'1 and is substantially parallel with the curved surface portion 63A.

In this structure, the axis of center of gravity in the probe 21A is defined. The axis of center of gravity is an axis (a line) formed by connecting centers of gravity in respective cross sections crossing the extended direction of the probe 21A. The axis of center of gravity of the probe 21A in the straight portion 42A is referred to as axis of center of gravity G'1, and the axis of center of gravity of the probe 21A in the curved portion 43A is referred to as axis of center of gravity G'2. In the straight portion 42A, the axis of center of gravity G'1 extends through the center of the probe 21A. Accordingly, the axis of center of gravity G'1 substantially agrees with the longitudinal axis C'. Specifically, the axis of center of gravity G'1 is extended in the center of the probe 21A along the longitudinal axis C'.

In the present comparative example, the curved surface portion 53A is formed in substantially parallel with the curved surface portion 63A. Accordingly, the axis of center of gravity G'2 of the curved portion 43A extends through the central position between the curved surface portion 53A and the curved surface portion 63A (imaginary curved surface V'). For this reason, the axis of center of gravity G'2 is provided in the state of going toward the first width direction as it extends from the proximal side toward the distal side. The distance between the axis of center of gravity G'2 and the longitudinal axis C' is referred to as distance L2. The distance L2 indicates quantity of fluctuations of the center of gravity in the curved portion 43A with respect to the axis of center of gravity G'1 (longitudinal axis C') of the straight portion 42A. In the curved portion 43A, the distance L2 from the longitudinal axis C' increases from the proximal side toward the distal side. Accordingly, the center of gravity of the curved portion 43A varies widely with respect to the center of gravity of the straight portion 42A from the distal side toward the proximal side. As in the present comparative example, when the axis of center of gravity of the probe 21A varies in the curved portion 43A, such variation may influence the stability of ultrasonic vibrations transmitted with the probe 21A serving as the vibration transmitter.

By contrast, the probe 21 of the present embodiment is provided with the first portion 57 and the second portion 58 in the first side surface 51 in the curved portion 43. FIG. 4 illustrates the state of the axis of center of gravity of the probe 21 in the present embodiment. FIG. 4 also illustrates the state of the axis of center of gravity G'2 in the case where neither first portion 57 nor second portion 58 is provided like the comparative example described above. As illustrated in FIG. 4, the axis of center of gravity G1 serves as the axis of center of gravity in the straight portion 42, and the axis of center of gravity G2 serves as the axis of center of gravity in the curved portion 43. Also in the present embodiment, the longitudinal axis C extends through the center of the straight portion 42. For this reason, the axis of center of gravity G1 of the straight portion 42 substantially agrees with the longitudinal axis C.

In the present embodiment, the curved surface portion 53 is provided with the first portion 57. In the first portion 57, the curved surface portion 53 is positioned on the second width direction side of the imaginary curved surface V, that is, a side opposite to the side toward which the curved portion 43 is curved. For this reason, in the portion provided with the first portion 57 in the probe 21, the axis of center of gravity G2 is positioned on the second width direction side of the axis of center of gravity G'2. Specifically, in the portion provided with the first portion 57, the probe 21 is asymmetrical in the width direction with respect to the central position between the curved surface portion 63 and the imaginary curved surface V. Because the axis of center of gravity G2 is positioned on the second width direction side of the axis of center of gravity G'2, the axis of center of gravity G2 has the smaller distance L2 from the longitudinal axis C than that of the axis of center of gravity G'2, in the portion provided with the first portion 57. As described above, the length of the distance L2 between the axis of center of gravity G2 and the longitudinal axis C indicates magnitude of fluctuations of the center of gravity with respect to the straight portion 42. For this reason, fluctuations of the center of gravity in the probe 21 of the present embodiment are smaller than fluctuations of the center of gravity in the probe 21A of the comparative example.

As described above, the present embodiment provided with the first portion 57 reduces (suppresses) fluctuations (shift) of the center of gravity in the curved portion 43 with respect to the straight portion 42, in comparison with the case where no first portion 57 is provided like the comparative example. Suppression of fluctuations of the center of gravity in the curved portion secures stability of ultrasonic vibrations transmitted with the probe 21 serving as the vibration transmitter, and secures treatment performance of the energy treatment instrument 2 including the probe 21. Specifically, this structure secures stability of ultrasonic vibrations transmitted with the probe 21, even in the case where the distal portion (treatment portion 23) of the probe 21 is provided with the curved portion 43.

In addition, the stress caused by ultrasonic vibrations becomes zero in the antinode of longitudinal vibrations, and becomes maximum in the node of the longitudinal vibrations. In addition, the stress caused by ultrasonic vibrations increases toward the node. Accordingly, influence of fluctuations of the center of gravity on stability of vibrations gradually increases from the antinode toward the node of longitudinal vibrations. For this reason, fluctuations of center of gravity in the probe 21 are preferably small in a region distant from the antinode. As described above, in the predetermined vibration mode, the most distal node N1 in the nodes of longitudinal vibrations is positioned on the proximal side of the treatment portion 23 provided with the curved portion 43 in the probe 21. For this reason, the curved portion 43 is desired to have small fluctuations of the center of gravity in the proximal region close to the node N1.

In the present embodiment, the proximal position of the first portion 57 substantially agrees with the reference position H1 serving as the proximal position of the curved portion 43. Specifically, the first portion 57 is provided to extend from the proximal position toward the distal side of the curved portion 43. For this reason, fluctuations of the center of gravity of the probe 21 is suppressed in the proximal region of the curved portion 43, that is, the portion close to the node N1 in the curved portion 43. Accordingly, the present embodiment effectively reduces the influence of fluctuations of center of gravity of the probe 21 on vibrations.

Also in the second portion 58, the curved surface portion 53 is positioned on the second width direction side of the imaginary curved surface V, that is, on a side opposite to the side toward which the curved portion 43 is curved. For this reason, the axis of center of gravity G2 is positioned on the second width direction side of the axis of center of gravity G'2, also in the portion provided with the second portion 58 in the probe 21. Accordingly, this structure suppresses fluctuations of the center of gravity in the curved portion 43 also in the portion provided with the second portion 58, in comparison with the comparative example, like the portion provided with the first portion 57.

Besides, the second portion 58 is formed in the state in which the distance L1 from the imaginary curved surface V decreases as it extends from the proximal side toward the distal side. For this reason, in the portion provided with the second portion 58, the curved surface portion 53 is greatly curved with respect to the extended surface 52, in comparison with the portion provided with the first portion 57. This structure secures treatment performance and visibility with the second portion 58 of the curved portion 43, also in the structure in which the curved portion 43 is provided with the first portion 57.

In addition, in the second portion 58, the distance L2 between the axis of center of gravity G2 and the longitudinal axis C increases as the second portion 58 extends from the distal side toward the proximal side. For this reason, in the portion provided with the second portion 58, fluctuations of the axis of center of gravity G2 from the axis of center of gravity G1 increase toward the distal side. In the predetermined vibration mode, the distal end of the probe 21 serves as the antinode, and the most distal node N1 is positioned on the proximal side of the curved portion 43. For this reason, in the curved portion 43, the influence of fluctuations of the center of gravity on stability of vibrations decreases toward the distal side. Accordingly, in the portion provided with the second portion 58, the influence on stability of vibrations is small even when fluctuations of the center of gravity increase.

To suppress fluctuations of the center of gravity in the curved portion 43, a possible solution is to move the axis of the center of gravity G2 in the second width direction by reducing the curve of the curved surface portion 63 provided outside the curve of the curved portion 43 with respect to the extended surface 62. In this case, however, there is the possibility that neither treatment performance nor visibility is secured even when the curved portion 43 is provided. In the present embodiment, the curved surface portion 53 inside the curve of the curved portion 43 is provided with the first portion 57. This structure suppresses fluctuations in center of gravity in the curved portion 43 while the curved shape of the curved surface portion 63 is maintained in a shape securing treatment performance and visibility.

In an embodiment, high-frequency current (high-frequency energy) is supplied to the living tissue, in addition to ultrasonic vibrations. In this case, each of the treatment portion 23 and the jaw 28 is provided with an electrode (first electrode and second electrode), and the power unit 8 is provided with another energy output source (not illustrated) separate from the energy output source 9. Electric energy (high-frequency electric energy) is supplied to each of the electrodes described above from the energy output source, a high-frequency current flows between the electrodes through the living tissue grasped between the treatment portion 23 and the jaw 28. In this manner, the living tissue is coagulated (sealed).

Figure 8:
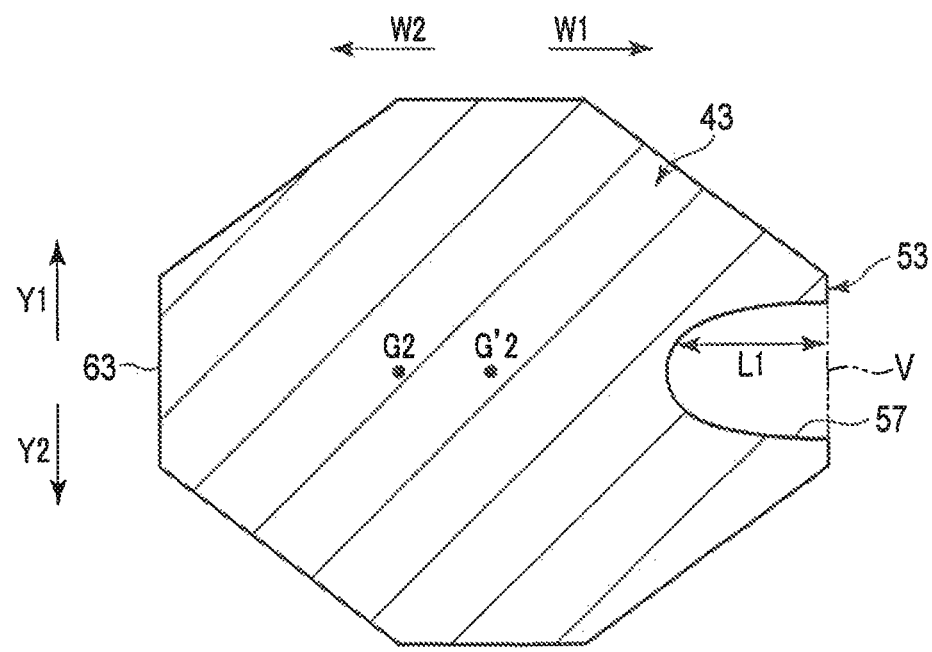
FIG. 8 is a diagram schematically illustrating a curved portion at a cross section substantially perpendicular to the extending direction.

The curved surface portion 53 can have a structure in which each of the first portion 57 and the second portion 58 is provided over the whole probe 21 in the opening/closing directions of the end effector 6, but the structure is not limited thereto. FIG. 8 is a diagram illustrating the curved portion 43 in a cross section crossing (substantially perpendicular to) the extended direction of the curved portion 43, in the portion provided with the first portion 57 in a first modification. As illustrated in FIG. 8, in the present modification, the curved surface portion 53 is provided with the first portion 57 and the second portion 58, in only a part of the portion in the opening/closing directions of the end effector 6 serving as the direction crossing the curved direction of the curved portion 43 and the longitudinal axis C. Specifically, the curved surface portion 53 includes a portion extending away from the imaginary curved surface V in the second width direction, in only a part of the portion in the opening/closing directions of the end effector 6. For this reason, the curved surface portion 53 is recessed in the second width direction with respect to the imaginary curved surface V, in the opening/closing directions of the end effector 6 in the portion provided with the first portion 57 and the second portion 58. The curved surface portion 53 substantially agrees with the imaginary curved surface V, in a portion not provided with the first portion 57 or the second portion 58 in the opening/closing directions of the end effector 6.

In the portion provided with the first portion 57 or the second portion 58, the probe 21 is asymmetrical in the width direction with respect to the central position between the curved surface portion 63 and the imaginary curved surface V, and the axis of center of gravity G2 is positioned on the second width direction side of the axis of center of gravity G'2. For this reason, fluctuations of center of gravity in the probe 21 are smaller than fluctuations of center of gravity in the probe 21A.

In addition, a plurality of first portions 57 and/or a plurality of second portions 58 may be provided apart from each other in the opening/closing directions of the end effector 6.

Figure 9:
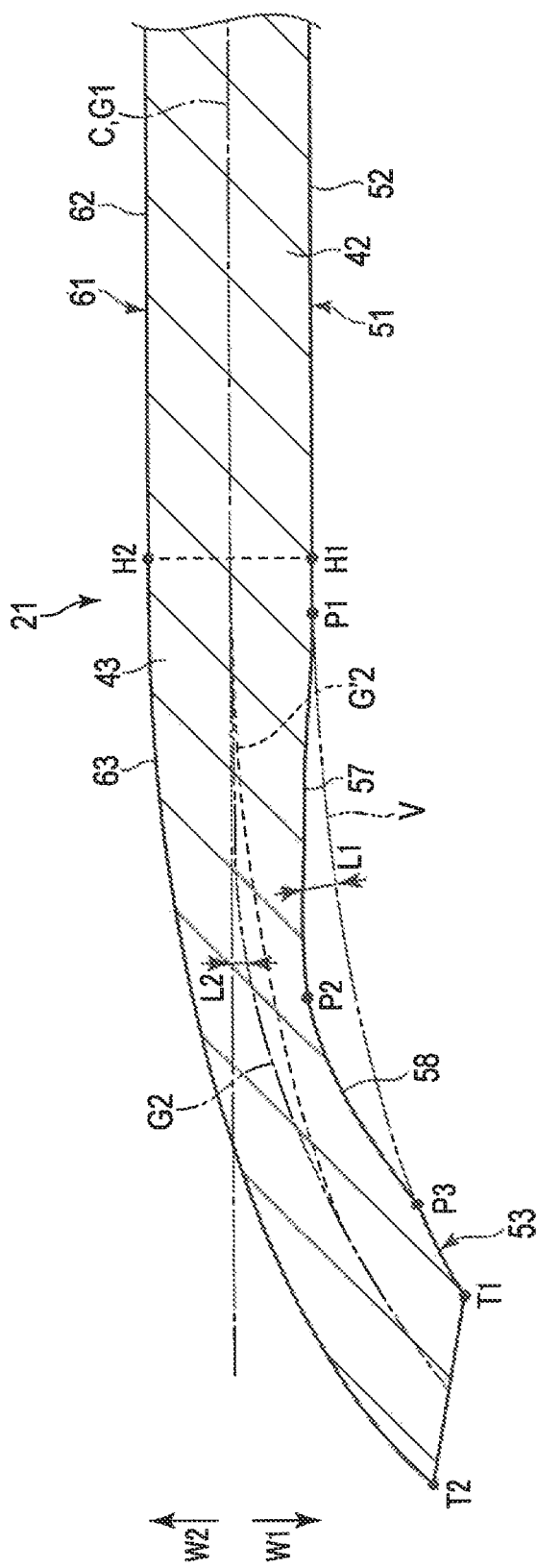
FIG. 9 is a cross-sectional view schematically illustrating a distal portion of a probe.

FIG. 9 illustrates the distal portion of the probe 21 in a cross section extending along the longitudinal direction and the width direction of the probe 21. As illustrated in FIG. 9, the position P1 serving as a proximal position of the first portion 57 is located on the distal side of the reference position H1. Specifically, the first portion 57 is provided on the distal side of the reference position H1. In a portion between the reference position H1 and the position P1, the curved surface portion 53 is formed in substantially parallel with the curved surface portion 63. For this reason, in the portion between the reference position H1 and the position P1, the curved surface portion 53 substantially agrees with the imaginary curved surface V, and the distance L1 between the first side surface 51 and the imaginary curved surface V is 0.

In a portion provided with the first portion 57 and the second portion 58, the probe 21 is asymmetrical in the width direction with respect to the central position between the curved surface portion 63 and the imaginary curved surface V, and the axis of center of gravity G2 is positioned on the second width direction side of the axis of center of gravity G'2. For this reason, fluctuations of center of gravity in the probe 21 are smaller than fluctuations of center of gravity in the probe 21A.

[Third Modification]

Figure 10:
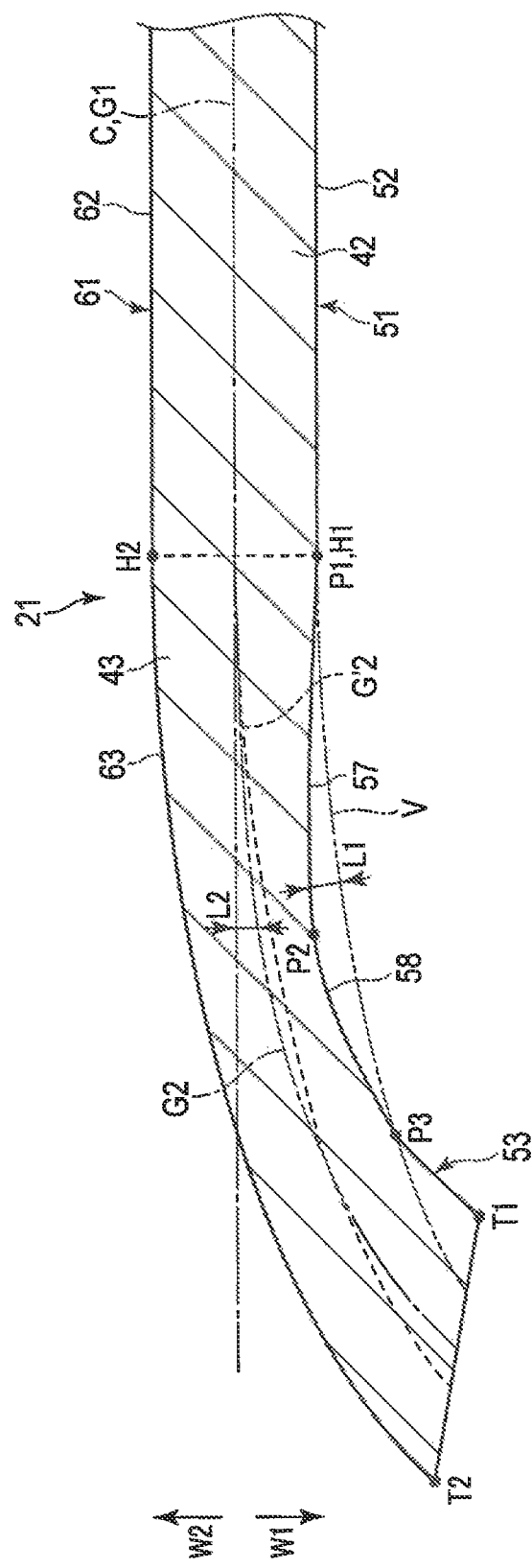
FIG. 10 is a cross-sectional view schematically illustrating a distal portion of a probe.

FIG. 10 is a diagram illustrating a distal portion of the probe 21 according to a third modification of the present embodiment. FIG. 10 illustrates the probe 21 in a cross section extending along the longitudinal direction and the width direction of the probe 21. As illustrated in FIG. 10, in the present modification, the curved surface portion 53 is positioned on the first width direction side of the imaginary curved surface V, that is, the side toward which the curved portion 43 is curved, in a portion between the position P3 and the curve distal end T1. For this reason, the portion between the position P3 and the curve distal end T1 is greatly curved with respect to the first portion 57 and the second portion 58. This structure further improves treatment performance and visibility.

In addition, in the predetermined vibration mode, the distal end of the probe 21 serves as the antinode, and the most distal node N1 is positioned on the distal side of the curved portion 43. For this reason, in the curved portion 43, influence of fluctuations of center of gravity on stability of vibrations is reduced toward the distal side. This structure suppresses influence on stability of vibrations, even when the curved surface portion 53 is greatly curved and fluctuations of center of gravity increase in the range between the position P3 and the curve distal end T1.

[Fourth Modification]

FIG. 11 is a diagram illustrating a distal portion of the probe 21 according to a fourth modification of the present embodiment. FIG. 11 illustrates the probe 21 in a cross section extending along the longitudinal direction of the distal portion of the probe 21 and the width direction of the probe 21. As illustrated in FIG. 11, in the present modification, a portion between the position P3 and the curve distal end T1 is positioned on the second width direction side of the imaginary curved surface V, that is, on a side opposite to the side toward which the curved portion 43 is curved. Accordingly, the curved surface portion 53 is positioned on the second width direction side of the imaginary curved surface V, in a portion on the distal side of the reference position H1.

In the present modification, also in the portion between the position P3 and the curve distal end T1, the curved surface portion 53 is positioned on the second width direction side of the imaginary curved surface V. For this reason, also in the portion between the position P3 and the curve distal end T1, the axis of center of gravity G2 is positioned on the second width direction side of the axis of center of gravity G'2, in the same manner as the portion provided with the first portion 57 and the second portion 58. For this reason, also in the present modification, fluctuations of center of gravity in the probe 21 are smaller than fluctuations of center of gravity in the probe 21A of the comparative example.

The position P3 serving as the distal position of the second portion 58 may agree with the curve distal end T1. In this case the second portion 58 extends toward the distal end of the curved surface portion 53, and the curve distal end T1 is served as the distal end of the second portion 58.

In the above embodiment and the like, the second portion 58 connects with the distal side of the first portion 57, but the structure is not limited thereto. For example, a portion having the fixed distance L1 from the imaginary curved surface V may be provided between the first portion 57 and the second portion 58. In this case, the portion between the first portion 57 and the second portion 58 is positioned on the second width direction side of the imaginary curved surface V, that is, on a side opposite to the side toward which the curved portion 43 is curved.

The probe 21 of the embodiment and the like described above is also applicable to other structures using an ultrasonic probe (vibration transmitter) provided with a distal portion including a curved portion. For example, in an embodiment, the probe 21 is also applicable as an ultrasonic probe in an ultrasonic treatment instrument provided with no jaw. In such an ultrasonic treatment instrument, the distal portion of the ultrasonic probe (probe 21) to which ultrasonic vibrations are transmitted is directly caused to abut against the treated target, such as the bone, to perform treatment to resect the treated target, such as the bone.

Also in such an ultrasonic treatment instrument, the curved portion can be provided with the first portion (57).

This structure suppresses fluctuations of center of gravity in the curved portion, and secures stability of ultrasonic vibrations in the ultrasonic probe.

The vibration transmitter (21) according to the embodiment and the like (excluding the comparative example) described above is a vibration transmitter (21) extended along a longitudinal axis (C), including a proximal end and a distal end, and transmitting ultrasonic vibrations from the proximal end to the distal end, comprising: a straight portion (42) provided on the vibration transmitter (21) and extended along the longitudinal axis (C); a curved portion (43) provided on a distal side of the straight portion (42) in the vibration transmitter (21), and curved in a direction crossing the longitudinal axis (C) with respect to the straight portion (42); a first curved surface (53) provided on an external surface of the curved portion (43) and facing a side toward which the curved portion (43) is curved; a second curved surface (63) provided on the external surface of the curved portion (43) and facing a side opposite to the side toward which the curved portion (43) is curved; and a first portion (57) provided on the first curved surface (53), extended on a side opposite to the side toward which the curved portion (43) is curved with respect to an imaginary curved surface (V), and having a distance (L1) from the imaginary curved surface (V), the distance (L1) increasing from the proximal side toward the distal side, the imaginary curved surface (V) extending through the first curved surface (53) at a curve start position of the curved portion (43) and defined in parallel with the second curved surface (63).

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A vibration transmitter that extends along a longitudinal axis and includes a proximal end and a distal end, the vibration transmitter being configured to transmit ultrasonic vibrations from the proximal end to the distal end, the vibration transmitter comprising:
   a straight portion that extends along the longitudinal axis on a proximal side of the vibration transmitter;
   a curved portion provided on a distal side of the vibration transmitter and curved in a direction that intersects with the longitudinal axis, the curved portion including:
      a first curved surface provided on a first surface of the curved portion that faces a side that the curved portion is curved towards;
      a second curved surface provided on a second surface of the curved portion that faces a side opposite to the side that the curved portion is curved towards; and
      a first portion provided on the first curved surface, the first portion extending towards the side opposite the side that the curved portion is curved towards from an imaginary curved surface, the imaginary curved surface extending from the first curved surface to a curved start position where the straight portion contacts the curved portion, the imaginary curved surface being parallel with the second curved surface, a distance between the first portion and the imaginary curved surface increasing from the proximal side of the vibration transmitter toward the distal side, wherein:

a distal-most node of vibrations in a predetermined vibration mode is positioned on a proximal side of the curved portion; and the first curved surface further includes a second portion provided on the distal side relative to the first portion, the second portion extending towards the side opposite to the side that the curved portion is curved towards from the imaginary curved surface, and a distance between the second portion and the imaginary curved surface decreasing from the proximal side toward the distal side.

2. The vibration transmitter according to claim 1, wherein the first portion is provided over an entirety of the curved portion in a direction that intersects with a curved direction of the curved portion and the longitudinal axis.

3. The vibration transmitter according to claim 1, wherein a proximal end of the first portion is positioned at a proximal position of the curved portion.

4. The vibration transmitter according to claim 1, wherein:
the second curved surface is an arc-shaped curved surface, the arc-shaped curved surface having a central point on the side that the curved portion is curved towards, and
the imaginary curved surface is an arc-shaped curved surface, a distance between the imaginary curved surface and the central point being smaller than the distance between the second curved surface and the central point.

5. The vibration transmitter according to claim 1, further comprising:
a treatment portion treating a living tissue, part of the straight portion and the curved portion being provided in the treatment portion, and wherein
the distal-most node of vibrations in the predetermined vibration mode is positioned on the proximal side relative to the treatment portion.

6. The vibration transmitter according to claim 1, wherein a part of the first curved surface coincides with the imaginary curved surface.

7. An ultrasonic treatment instrument comprising:
the vibration transmitter of claim 1; and
a jaw configured to open and close with respect to a distal portion of the vibration transmitter.

8. The ultrasonic treatment instrument according to claim 7, wherein:
the distal portion of the vibration transmitter includes a first electrode,
the jaw includes a second electrode, and
each of the first electrode and the second electrode is supplied with high-frequency electric energy.

9. The ultrasonic treatment instrument according to claim 7, wherein the first curved surface is provided over an entirety of the curved portion.

10. The ultrasonic treatment instrument according to claim 9, wherein the curved portion is curved in a direction intersecting the opening and closing directions of the jaw and the longitudinal axis direction of the straight portion.

11. An ultrasonic treatment instrument comprising:
a vibration transmitter that extends along a longitudinal axis and includes a proximal end and a distal end, the vibration transmitter being configured to transmit ultrasonic vibrations from the proximal end to the distal end, the vibration transmitter comprising:
a straight portion that extends along the longitudinal axis on a proximal side of the vibration transmitter;
a curved portion provided on a distal side of the vibration transmitter and curved in a direction that intersects with the longitudinal axis, the curved portion including:
a first curved surface provided on a first surface of the curved portion that faces a side that the curved portion is curved towards;
a second curved surface provided on a second surface of the curved portion that faces a side opposite to the side that the curved portion is curved towards; and
a first portion provided on the first curved surface, the first portion extending towards the side opposite the side that the curved portion is curved towards from an imaginary curved surface, the imaginary curved surface extending from the first curved surface to a curved start position where the straight portion contacts the curved portion, the imaginary curved surface being parallel with the second curved surface, a distance between the first portion and the imaginary curved surface increasing from the proximal side of the vibration transmitter toward the distal side; and
an ultrasonic transducer converting electric energy into ultrasonic vibrations, and transmitting the ultrasonic vibrations to the vibration transmitter; and
a shaft extended along the longitudinal axis, wherein:
a distal-most node of vibrations in a predetermined vibration mode is positioned on a proximal side of the curved portion; and
the vibration transmitter is configured to be inserted through the shaft such that:
the straight portion projects from the shaft, and
the distal-most node of vibrations is positioned inside the shaft.

* * * * *